US010633597B2

(12) United States Patent
Lacombe et al.

(10) Patent No.: US 10,633,597 B2
(45) Date of Patent: Apr. 28, 2020

(54) USE OF ZEOLITE NU-86 FOR NAPHTHA CATALYTIC CRACKING

(71) Applicant: IFP Energies nouvelles, Rueil-Malmaison (FR)

(72) Inventors: Sylvie Lacombe, Vernaison (FR); Bogdan Harbuzaru, Simandres (FR); Ludovic Raynal, Oullins (FR); Bertrand Fanget, Vienne (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/091,796

(22) PCT Filed: Apr. 4, 2017

(86) PCT No.: PCT/EP2017/057960
§ 371 (c)(1),
(2) Date: Oct. 5, 2018

(87) PCT Pub. No.: WO2017/174566
PCT Pub. Date: Oct. 12, 2017

(65) Prior Publication Data
US 2019/0161685 A1 May 30, 2019

(30) Foreign Application Priority Data
Apr. 8, 2016 (FR) ..................... 16 53089

(51) Int. Cl.
| *C10G 11/05* | (2006.01) |
| *C10G 35/06* | (2006.01) |
| *B01J 21/04* | (2006.01) |
| *B01J 21/16* | (2006.01) |
| *B01J 29/70* | (2006.01) |
| *B01J 29/80* | (2006.01) |
| *B01J 29/85* | (2006.01) |
| *B01J 37/00* | (2006.01) |
| *B01J 37/08* | (2006.01) |
| *B01J 37/30* | (2006.01) |
| *B01J 37/34* | (2006.01) |
| *C07C 4/06* | (2006.01) |
| *C10G 11/18* | (2006.01) |
| *B01J 29/06* | (2006.01) |

(52) U.S. Cl.
CPC .............. *C10G 11/05* (2013.01); *B01J 21/04* (2013.01); *B01J 21/16* (2013.01); *B01J 29/70* (2013.01); *B01J 29/80* (2013.01); *B01J 29/85* (2013.01); *B01J 37/0018* (2013.01); *B01J 37/08* (2013.01); *B01J 37/30* (2013.01); *B01J 37/343* (2013.01); *C07C 4/06* (2013.01); *C10G 11/18* (2013.01); *C10G 35/065* (2013.01); *B01J 2029/062* (2013.01); *B01J 2229/16* (2013.01); *B01J 2229/186* (2013.01); *B01J 2229/37* (2013.01); *C07C 2521/04* (2013.01); *C07C 2527/18* (2013.01); *C07C 2529/70* (2013.01); *C10G 2300/104* (2013.01); *C10G 2300/1044* (2013.01); *C10G 2300/1048* (2013.01); *C10G 2300/70* (2013.01); *C10G 2400/20* (2013.01); *Y02P 30/10* (2015.11)

(58) Field of Classification Search
CPC .. C10G 11/05; C10G 11/18; C10G 2300/104; C10G 2300/1044; C10G 2300/70; C10G 2400/20; B01J 21/04; B01J 21/16; B01J 37/0018; B01J 37/08; B01J 37/30; B01J 37/343; B01J 29/70; B01J 29/80; B01J 29/85; B01J 2229/16; B01J 2229/186; B01J 2229/37; B01J 2029/062; C07C 4/06; C07C 2521/04; C07C 2527/18; C07C 2529/70
See application file for complete search history.

(56) References Cited

U.S. PATENT DOCUMENTS

| 5,108,579 A | 4/1992 | Casci |
| 5,932,088 A * | 8/1999 | Benazzi ................. C10G 45/64 208/109 |
| 7,579,513 B2 | 8/2009 | Duplan |
| 2007/0010699 A1 | 1/2007 | Choi |
| 2007/0167662 A1 * | 7/2007 | Duplan ..................... C07C 4/06 585/653 |

(Continued)

FOREIGN PATENT DOCUMENTS

FR          2859994 A1      3/2005

OTHER PUBLICATIONS

Kubo et al. ("Comparison of steaming stability of Cu—ZSM-5 with those of Ag—ZSM-5, P/H—ZSM-5, and H—ZSM-5 zeolites as naphtha cracking catalysts to produce light olefin at high temperatures" Applied Catalysis A: General 489 (2015) 272-279) (Year: 2014).*

(Continued)

*Primary Examiner* — In Suk C Bullock
*Assistant Examiner* — Jason Y Chong
(74) *Attorney, Agent, or Firm* — Millen, White, Zelano and Branigan, P.C.

(57) ABSTRACT

The invention relates to a process for the catalytic cracking of a gasoline feedstock for the production of light olefins, in which said gasoline feedstock is brought into contact with a catalyst comprising at least one zeolite NU-86, alone or in a mixture with at least one other zeolite, at a temperature comprised between 500 and 700° C., at an absolute pressure comprised between 10 and 60 MPa, and with a contact time of the feedstock on said catalyst comprised between 10 milliseconds and 100 seconds.

17 Claims, No Drawings

(56) References Cited

U.S. PATENT DOCUMENTS

2014/0209508 A1    7/2014   Hassan

OTHER PUBLICATIONS

International Search Report PCT/EP2017/057960 dated Jun. 14, 2017.
Corma A et al: "The role of pore topology on the behaviour of FCC zeolite additives", Applied Catalysis A: Gen, Elsevier, Amsterdam, NL, vol. 187, No. 2, Oct. 25, 1999 (Oct. 25, 1999), pp. 245-254, XP004271976, ISSN: 0926-860X.

* cited by examiner

USE OF ZEOLITE NU-86 FOR NAPHTHA CATALYTIC CRACKING

TECHNICAL FIELD

The invention relates to a process for the production of light olefins by catalytic cracking of gasoline, preferably originating from the direct distillation of petroleum, called "straight run" naphtha. The objective of the process according to the invention is to maximize the yields of light olefins, in particular ethylene, propylene and butenes as well as BTX by cracking naphtha preferably comprising a high paraffin content.

In fact, ethylene and propylene, light olefinic hydrocarbons with two or three carbon atoms per molecule respectively, are important chemical intermediates for the production of molecules of interest such as polyethylene and polypropylene, which are two of the plastics most commonly used nowadays, in particular in packaging. Other uses for propylene and ethylene comprise the production of vinyl chloride, ethylene oxide, ethylbenzene and alcohol.

Steam cracking, pyrolysis of hydrocarbon-containing cuts or FCC or "fluid catalytic cracking" technology produce practically all of the ethylene and propylene. The hydrocarbons used as raw material for the production of light olefins comprise natural gas, condensates of natural gas, liquid hydrocarbon-containing cuts originating from the distillation of petroleum and carbon-containing materials including coal, recycled plastics or any organic matter.

Thus, the relatively recent interest in the implementation of the process for the production of light olefins by catalytic cracking of naphtha feedstock derives from the need to have light olefins available for petrochemistry, in addition to the steam cracking of naphtha, which is the traditional source, owing to:
  the presence of an ever increasing imbalance between the production of propylene and the production of ethylene, especially with the success of steam crackers using an ethane feedstock, which produce less propylene,
  the anticipated availability of naphtha owing to a reduction in the consumption of gasoline, the introduction of alternative motor fuels, and the massive arrival of condensates (e.g. shale) on the market,
  the wish to reduce the energy costs of propylene production and reduce $CO_2$ emissions that follow from an operation at lower temperature than that of steam cracking of naphtha, as the catalytic activity reduces the need for high temperatures.

A new method commonly called "NCC" for "Naphtha Catalytic Cracking", has been developed for the production of light olefins. It is generally carried out in the presence of a zeolite catalyst at a temperature of the order of 600° C. to maximize the yield of light olefins.

The presence of a catalyst in this process for the catalytic cracking of naphtha feedstock makes it possible to:
  produce far more propylene per tonne of naphtha than with steam cracking;
  improve the upgrading of naphtha to products with high added value, the demand for which is constantly increasing, and in particular to propylene, ethylene and BTX,
  crack naphtha at a temperature that is 150 to 200° C. lower than that used for thermal steam cracking that is generally carried out at between 800 and 900° C., so as to have a lower energy cost of production of propylene and ethylene while reducing $CO_2$ emissions.

Most of these NCC processes use a zeolitic acid catalyst based on ZSM-5. However, in the harsh conditions of the naphtha catalytic cracking process, which is generally carried out at a temperature of at least 600° C. and in the presence of steam introduced into the reactor, the acid catalyst based on zeolite ZSM-5 is subject to high deactivation on the one hand by dealumination of its crystal lattice (irreversible deactivation) which leads to an at least partial collapse of its structure, and on the other hand owing to a reduction in the acid sites of the zeolite due to the interaction of water with said acid sites, resulting in a rapid decrease in catalyst activity.

Today, only KBR has adopted a position on this market, offering the "ACO" process, co-developed with the company SK Innovation and henceforth marketed under the name "K-COT", using a modified type ZSM-5 catalyst and a slightly adapted FCC technology, with max.-propylene as the announced target.

However, extensive prior art exists regarding this subject.

PRIOR ART

The vast majority of the documents of the prior art (journals or patents) on catalysts for NCC concern zeolite ZSM-5 (MFI structure), which makes it possible to obtain the best performance compared to the many other zeolite structures tested. However, it still lacks stability.

Many documents disclose the use of zeolite ZSM-5 optionally combined with various dopants. One of the objectives sought with the addition of one or more dopants is to stabilize the aluminium atoms of the zeolite network so as to limit dealumination under the operating conditions of NCC, dealumination being promoted by the high temperature and the presence of steam. A second objective is an appropriate modification of the acidity of the catalysts, generally passivation of the strongest acid sites, so as to improve the selectivity of the process.

The journal article by Rahimi et al. (Applied Catalysis A, 398(2011)1-17) examines all the dopants of ZSM-5 studied in the literature on naphtha catalytic cracking for the production of light olefins. The best yields of light olefins are obtained by combining ZSM-5 with phosphorus, magnesium, calcium and copper.

Kubo et al. (Catalysis Communication 29(2012)162, Applied Catalysis A 489(2015)272) published on zeolite ZSM-5 modified with copper by cation exchange, which they find much more stable in hydrothermal conditions and more active than a P-ZSM-5.

Patent application WO2007/043741 by SK Corporation discloses the production of light olefins starting from hydrocarbon-containing feedstock with a high yield and high selectivity using various catalyst formulations comprising a zeolite comprising the Si—OH—Al group in its network, having a pore size between 10 and 100 Å, an Si/Al molar ratio between 1 and 300 and preferably selected from ZSM-5, ferrierite, ZSM-11, mordenite, zeolite beta, zeolite L, MCM-41, SBA-15 and/or zeolite Y combined with various dopants such as metal salts of Mg, Ca, Sr, Ba, Ti, V, Cr, Mn, Fe, Co, Ni, Cu, B, Al, Ga, In, Ti, Sn, Pb, Sb and Bi and a phosphorus-containing compound. It is demonstrated that the catalytic composition used has a stable structure at high temperature and in the presence of steam and gives a high yield and high selectivity for ethylene and propylene.

Patent application US2011/0039688 by SK Energy describes a naphtha catalytic cracking process using a catalyst containing zeolite ZSM-5, clay and an inorganic oxide, said catalyst being promoted with manganese and phosphorus, and optionally lanthanum, and is formed by atomization of the mixture comprising the various components.

U.S. Pat. No. 6,548,725 by BP describes a process for the production of light olefins by naphtha catalytic cracking using a catalyst comprising a zeolite of the pentasil type, for example ZSM-5 or ZSM-11 with an Si/Al ratio between 10 and 400, in which from 0.1 to 10% by weight of phosphorus and 0.1 to 10% by weight of at least one promoter selected from gallium (Ga), germanium (Ge) and tin (Sn) are incorporated, for example by impregnation. Said process makes it possible to convert the naphtha feedstock to light olefins while avoiding the production of a significant quantity of undesirable products such as aromatics or methane.

Patent application WO2014/181293 by Saudi Basic Industries Corporation describes a process for the production of light olefins by naphtha catalytic cracking using a catalyst comprising a modified zeolite that has undergone a step of desilication by being brought into contact with a basic compound and then a step of realumination by being brought into contact with a realuminating agent, said modified zeolite then optionally being doped with iron (Fe), titanium (Ti), barium (Ba) or tungsten (W). The only zeolite exemplified is ZSM-5. However, zeolites ZSM-8, ZSM-11, ZSM-12, ZSM-22, ZSM-23, ZSM-35, ZSM-38, ZSM-48, ZSM-57 and beta are also mentioned.

Other documents describe the use of catalysts based on zeolite other than ZSM-5 for naphtha catalytic cracking.

U.S. Pat. No. 7,585,489 by UOP describes a process for the production of light olefins by naphtha catalytic cracking using a zeolite with channels containing 10 tetrahedral atoms (10 MR) that are not interconnected, preferably selected from zeolites ITQ-3, ZK-4, SSZ-23, EU-1, MCM-22, ZSM-23, ZSM-22 and ferrierite.

Patent applications US2003100439A and US2005182278A, respectively, describe the use of zeolite ITQ-7 of structural type ISV, and ITP-22 of structural type IWW for naphtha catalytic cracking.

U.S. Pat. No. 6,656,345 by ExxonMobil describes the use, in olefinic naphtha catalytic cracking, of one-dimensional zeolites the pore aperture of which is delimited by 8, 10 or 12 tetrahedral atoms. The preferred zeolites belong to the families MTW, TON, MTT or zeolite ZSM-48.

The applicant has demonstrated that the use of a catalyst comprising at least one zeolite NU-86 in a process for the catalytic cracking of a gasoline feedstock makes it possible to obtain an improved performance in terms of yield of light olefins relative to the use of a reference catalyst based on zeolite ZSM-5.

In fact, no document of the prior art discloses the use of a catalyst comprising at least one zeolite NU-86 alone or in a mixture for use in a process of catalytic cracking of a naphtha feedstock for the production of light olefins.

Only patent application FR2758567 describes the use, for fluidized bed catalytic cracking or FCC of heavy cuts such as for example vacuum gas oil, of a catalyst comprising at least one dealuminated zeolite NU-86 at least partly in acid form, at least one zeolite Y and at least one matrix, the zeolite NU-86 being used as an additive to the catalyst based on zeolite Y used conventionally in the FCC processes. The FCC process according to FR2758567 is carried out at a temperature between 400 and 800° C., at a pressure between 0.05 and 1 MPa with a weight ratio of catalyst to feedstock (C/O) between 0.5 and 50 and a contact time between 1 and 10000 milliseconds.

Patent FR2837199 describes a process for the production of propylene starting from a C4 and/or C5 olefinic feedstock from steam cracking and/or catalytic cracking, comprising a step of oligomerization of the C4 and/or C5 in order to obtain higher olefins followed by a step of catalytic cracking of the oligomers formed. The feedstock for the catalytic cracking step contains from 20 to 100% by weight of C8+ olefins and can also comprise 25 to 100% by weight of C6+ oligomers.

The catalysts used in the step of oligomerization and catalytic cracking can comprise a silica-alumina but are preferably acidic with shape selectivity and therefore comprise a zeolite selected from the structural types MEL, such as ZSM-11, MFI, such as ZSM-5, NES, EUO, FER, CHA, such as for example SAPO-34, MFS, MWW, or from zeolites NU-85, NU-88, IM-5 and NU-86.

A catalyst comprising a mixture of MFI type zeolite and the aforementioned zeolites can also be used in the steps of oligomerization and catalytic cracking, as well as a catalyst comprising a mixture of zeolite Y with one of the aforementioned zeolites.

NU-86 is therefore cited among several other zeolite structures and can be used alone or in a mixture with another zeolite of type MFI or FAU, both in the oligomerization catalyst and the catalytic cracking catalyst.

SUBJECT OF THE INVENTION

The invention relates to a process for the catalytic cracking of a gasoline feedstock for the production of light olefins in which said gasoline feedstock is brought into contact with a catalyst comprising at least one zeolite NU-86, alone or in a mixture with at least one other zeolite, at a temperature comprised between 500 and 700° C., at an absolute pressure comprised between 10 and 60 MPa, and with a contact time of the feedstock on said catalyst comprised between 10 milliseconds and 100 seconds.

One advantage of the present invention is that it provides a process for the catalytic cracking of a gasoline feedstock using a catalyst comprising at least one zeolite NU-86 alone or in a mixture with at least one other zeolite allowing the production of chemical intermediates and in particular making it possible to improve the yields of desired light olefins relative to the use of a catalyst used conventionally in NCC such as ZSM-5.

Another advantage of the present invention is that it provides a process for the catalytic cracking of a gasoline feedstock allowing the predominant production of propylene relative to the conventional processes of the prior art such as the steam cracking process (propylene/ethylene weight ratio less than 0.6). In particular, the process according to the invention allows the production of propylene and ethylene with a propylene/ethylene weight ratio at least greater than 0.7 and preferably at least greater than or equal to 1.

Another advantage of the present invention is that it provides a process for the catalytic cracking of a gasoline feedstock using a catalyst comprising at least one zeolite NU-86 alone or in a mixture, said catalyst having good hydrothermal stability under the conditions of catalytic cracking and making it possible to obtain light olefins and in particular ethylene and propylene with a high yield and good selectivity relative to the feedstock.

DESCRIPTION OF THE INVENTION

The invention relates to a process for the catalytic cracking of a gasoline feedstock for the production of light olefins in which said gasoline feedstock is brought into contact with a catalyst comprising at least one zeolite NU-86, alone or in a mixture with at least one other zeolite, at a temperature comprised between 500 and 700° C., at an absolute pressure comprised between 10 and 60 MPa and with a contact time between the feedstock and said catalyst comprised between 10 milliseconds and 100 seconds.

Hereinafter, by "light olefins" is meant the olefins having a number of carbon atoms between 2 and 4. Preferably, the light olefins produced by the process according to the invention are ethylene and propylene.

Feedstock

According to the invention, the feedstock used is a gasoline feedstock comprising and preferably consisting of hydrocarbon compounds having 4 to 15 carbon atoms, preferably 5 to 14 carbon atoms.

Preferably, said gasoline feedstock has an initial boiling point comprised between 20 and 100° C. and preferably comprised between 30 and 80° C. and preferably between 35 and 60° C. and a final boiling point comprised between 100 and 250° C. and preferably between 120 and 200° C. and preferably between 120 and 180° C.

Preferably, the gasoline feedstock used in the process according to the invention is essentially paraffinic, i.e. it comprises essentially iso- and n-paraffins. Preferably, said feedstock comprises paraffins having 4 to 11 carbon atoms and preferably 6 to 9 carbon atoms.

By "essentially paraffinic feedstock" is meant a gasoline feedstock comprising a content of paraffins (normal+iso) comprised between 50 and 90% by weight with respect to the total weight of said feedstock.

Preferably, the feedstock used in the process according to the invention comprises less than 20% by weight of olefins preferably having at least 6 and/or at least 8 carbon atoms and preferably less than 17% by weight of olefins and preferably less than 15% by weight of olefins.

Preferably, the gasoline feedstock used in the process according to the invention comprises a content of paraffins (normal+iso) comprised between 50 and 90% by weight and preferably between 60 and 80% by weight, a content of olefins comprised between 0 and 17% by weight and preferably between 0 and 15% by weight, a content of naphthenes comprised between 10 and 60% by weight and preferably between 20 and 50% by weight, a content of aromatics between 0 and 30% by weight and preferably between 0 and 15% by weight, the percentages by weight being expressed with respect to the total weight of said feedstock and the sum of the different components being equal to 100%.

Preferably, said gasoline feedstock can originate from the direct distillation of petroleum, in this case the feedstock is "straight run" naphtha and/or originating from one or more processes for the production of gasoline such as for example the fluidized bed catalytic cracking or "FCC" process, and/or from a process purge such as in isomerization processes. This feedstock is commonly given the designation "Naphtha".

Preferably, the gasoline feedstock used in the process according to the invention has not undergone a step of chemical change before being introduced into said process according to the invention. For example, said gasoline feedstock has not undergone an oligomerization step before being sent into the process according to the invention.

Said gasoline feedstock can optionally undergo a step of pre-processing of the hydrotreating type prior to its use in the process according to the invention, so as to limit or remove the nitrogen-containing and sulphur-containing impurities and the oxygen-containing derivatives.

Process

According to the invention, the process is a process for the production of light olefins by catalytic cracking of a gasoline feedstock, in which said feedstock is brought into contact with the catalyst as claimed at a temperature comprised between 500 and 700° C., preferably between 550 and 700° C., yet more preferably between 600 and 680° C., at a total absolute pressure comprised between 10 and 60 MPa and preferably between 10 and 50 MPa and preferably between 10 and 40 MPa and with a contact time between the feedstock and said catalyst comprised between 10 milliseconds and 100 seconds, preferably between 20 milliseconds and 20 seconds and preferably between 100 milliseconds and 4 seconds.

Preferably, said gasoline feedstock is brought into contact with said catalyst in a reactor operating with a fixed bed, with a moving bed or with a fluidized bed, and preferably with a fluidized bed.

The gasoline feedstock can advantageously be introduced into said reactor in co-current, in counter-current or in cross-currents.

The gasoline feedstock can optionally be introduced into the reactor mixed with a diluent preferably selected from an inert gas such as nitrogen and steam.

Preferably the diluent is introduced at a rate of an quantity representing 1 to 15% by weight, preferably 1 to 6% by weight and preferably between 1 and 5% by weight with respect to the total weight of said mixture comprising the diluent and the feedstock.

Preferably, the gasoline feedstock is introduced into the reactor in a mixture with steam.

The presence of steam makes it possible to lower the partial pressure of the gasoline feedstock that is thermodynamically unfavourable for the cracking reactions and to improve fluidization and heat transfer. Moreover, the presence of water also makes it possible to limit the reactions of hydrogen transfer that lead to the formation of aromatics and undesirable light alkanes such as methane, ethane and propane.

In the reactor, the gasoline feedstock is converted by catalytic cracking in the presence of the catalyst as claimed to light olefins and in particular to ethylene and propylene.

At the end of the process according to the invention, the effluent produced is advantageously separated to recover the light olefins and preferably ethylene and propylene.

The catalyst that leaves the reactor is also advantageously separated from the effluent produced by the process according to the invention, stripped and regenerated before being recycled to the reactor of the catalytic cracking process according to the invention.

Catalyst

According to the invention, the process uses a catalyst comprising at least one zeolite NU-86, alone or in a mixture.

In a preferred embodiment, said catalyst comprises at least one zeolite NU-86 in a mixture with at least one other zeolite selected from zeolites ZSM-5, ZSM-11, beta, Y, ferrierite, ZSM-22, ZSM-23, and EU-1 alone or in a mixture, and preferably from zeolites ZSM-5, ZSM-11, beta, Y and ferrierite alone or in a mixture.

When said catalyst comprises a mixture of zeolite NU-86 and at least one other zeolite, said catalyst advantageously comprises a content of NU-86 comprised between 60 and 99% by weight and preferably between 70 and 90% by weight with respect to the total weight of zeolites comprised in said mixture.

Zeolite NU-86

Zeolite NU-86 in the hydrogen form, denoted H-NU-86 and obtained by calcination and/or ion exchanges of the crude synthesized zeolite NU-86 as well as its manner of preparation are described in patent EP-0463768 A2. Said zeolite NU-86 is characterized by structural data of X-ray diffraction defined by Casci et al. in patent application EP463,768.

Zeolite NU-86 is generally synthesized in the presence of sodium cations and an organic structure-forming agent, which is either octamethonium dibromide or nonamethonium dibromide.

Zeolite NU-86 contains silicon and at least one element T selected from the group formed by aluminium, iron, gallium, boron, germanium; preferably T is aluminium.

The structural type of this zeolite has not yet been officially attributed by the synthesis commission of the IZA (International Zeolite Association). However, according to the works published at the 9th International Zeolite Conference by J. L. Casci, P. A. Box and M. D. Shannon ("Proceedings of the 9th International Zeolite Conference", Montreal 1992, Eds R. Von Ballmoos et al., 1993 by Butterworth) it appears that, according to its properties:

zeolite NU-86 possesses a three-dimensional microporous system;

this three-dimensional microporous system consists of straight channels the pore opening of which is delimited by 11 T-atoms (atoms in tetrahedral configuration: Si, Al, Ga, Fe etc.), straight channels delimited alternatively by openings with 10 and 12 T-atoms and sinusoidal channels also delimited alternatively by openings with 10 and 12 T-atoms.

The zeolite NU-86 used according to the invention has a Si/T molar ratio less than 150, preferably less than 100, preferably less than 50.

Methods of dealumination of NU-86 are also described in patent application FR2758567 filed by IFPEN.

The Si/Al ratio can be obtained during synthesis, without any subsequent modification treatment. It can also be obtained by the dealumination techniques known to a person skilled in the art, such as for example steam treatment, i.e. heat treatment under steam and/or acid treatment. Patent application EP 0,939,673 describes methods for carrying out dealumination of zeolite NU-86.

Zeolite NU-86 can be used in the preparation of the catalyst according to the invention in its crude form or at least partly, or preferably practically completely, in the acid form, i.e. in the hydrogen form ($H^+$), the sodium content preferably being such that the Na/T atomic ratio is less than 10%, preferably less than 5%, yet more preferably less than 1%.

The zeolite NU-86 contained in the catalyst used according to the invention can also advantageously be dealuminated or not dealuminated.

The dealumination step can advantageously be carried out before or after forming, optionally both before and after forming of said zeolite. In addition to dealuminating the zeolite and thus obtaining an acidity that is more suitable for the process implemented, these treatments also make it possible to stabilize the zeolite, before it is subjected in the reactor to harsh conditions that can alter the crystallographic structure of the zeolite.

Said zeolite can advantageously be dealuminated by at least one heat treatment carried out, optionally and preferably in the presence of steam, at a temperature generally comprised between 500 and 900° C., and optionally followed by at least one acid treatment with an aqueous solution of a mineral or organic acid. The calcination conditions in the presence of steam (temperature, pressure of steam and treatment time) as well as the conditions of post-calcination acid treatment (treatment time, concentration of the acid, nature of the acid used and the ratio of the volume of acid to the weight of zeolite), are adapted so as to obtain the desired level of dealumination. The number of cycles of heat treatment and acid treatment that are carried out can also be varied with the same aim.

The catalyst used in the process according to the invention can also advantageously comprise at least one binder selected from the group of the inorganic refractory oxides. Preferably said binder is advantageously selected from alumina, silica, silica-alumina, magnesia, titanium oxide, zirconia, clays and boron oxide, alone or in a mixture and preferably from silica, silica-alumina and clays, alone or in a mixture.

In a preferred embodiment, the catalyst used in the process according to the invention comprises, in percentage by weight:

from 20 to 80% by weight and preferably from 30 to 70% by weight of at least one binder, from 20 to 80% by weight and preferably from 30 to 65% by weight of at least one zeolite NU-86 and, from 0 to 50% by weight and preferably from 0 to 30% by weight of at least one zeolite selected from zeolites ZSM-5, ZSM-11, beta, Y, ferrierite, ZSM-22, ZSM-23 and EU-1 alone or in a mixture, from 0 to 12% by weight, preferably from 0 to 6% by weight and very preferably from 0 to 3% by weight of at least one doping element, the percentages being expressed with respect to the total weight of said catalyst and the sum of the contents of said elements being equal to 100%.

The catalyst utilized in the process according to the invention can advantageously be formed, by any technique known to a person skilled in the art, with the aim of achieving a catalyst morphology suitable for the catalytic cracking process. The catalyst can advantageously be in the form of extrudates, beads, pellets, or grains. Forming is preferably carried out by extrusion, by atomization, by spheronization, by "oil-drop" or by pelletization.

In all cases, preferably, the zeolite or zeolites are dispersed with the binder by the methods known to a person skilled in the art, for example co-grinding, ultrasonic treatment of the zeolite or zeolites and of the binder in suspension in a liquid or passage through high-shear equipment of the Ultra-Turrax type.

Preferably, the catalyst is in the form of grains with a size of less than 200 µm, preferably less than 130 µm, for utilization in a fluidized bed.

According to a preferred embodiment, the catalyst is formed by atomization or by granulation.

According to another preferred embodiment, said catalyst is formed by extrusion followed by a step of spheronization.

One or more dopants preferably selected from phosphorus (P), magnesium (Mg), sodium (Na), potassium (K), calcium (Ca), iron (Fe), boron (B), manganese (Mn), lanthanum (La), cerium (Ce), titanium (Ti), tungsten (W), molybdenum (Mo), copper (Cu), zirconium (Zr) and gallium (Ga) alone or in a mixture and preferably selected from phosphorus (P), magnesium (Mg), copper (Cu), calcium (Ca) and lanthanum (La) can optionally be introduced into said catalyst. The dopant can optionally be introduced on the zeolite before forming or on the already formed catalyst, preferably by any method known to a person skilled in the art, such as for example dry impregnation, excess impregnation, and ion exchange.

Preferably, the content of doping elements in said catalyst is comprised between 0 and 12% by weight with respect to the total weight of said catalyst, preferably from 0 to 6% by weight and very preferably from 0 to 3% by weight.

Preferably, the catalyst, before or after forming and/or before or after adding the doping element or elements, is subjected to at least one steam treatment at a temperature comprised between 500 and 850° C., preferably between 600 and 750° C., in the presence of from 2 to 100% of steam, preferably between 5 and 80% of steam, for a duration comprised between 15 minutes and 48 hours, preferably between 30 minutes and 24 hours.

The examples illustrate the invention without limiting its scope.

EXAMPLES

Example 1: Preparation of Catalyst NC1 (not According to the Invention)

The zeolite used is an $NH_4$-ZSM-5 supplied by Zeolyst with the trade reference CBV5020 having an Si/Al molar ratio=25.

Forming the Zeolite by Mixing-Extrusion

An aqueous suspension containing the zeolite is mixed with boehmite PURAL SB3 and kaolin. The composition as percentage dry weight is 40% zeolite, 30% kaolin and 30% alumina. After obtaining a homogeneous paste, the latter is extruded through a die and the extrudates are dried for 12 hours at 120° C. and calcined under an air flow for 2 hours at 550° C.

Post-Treatments

The extrudates are then subjected to steam treatment for 24 hours under a flow of 100% of steam at a flow rate of 1 litre per hour per gram of extrudates under NTP conditions at 800° C. Then the latter are ground and sieved in order to retain the 40-140 μm fraction. The catalyst thus obtained is called NC1.

Example 2: Preparation of Catalyst NC2 (not According to the Invention)

The zeolite used is an $NH_4$-ZSM-5 supplied by Zeolyst with the trade reference CBV5020 having an Si/Al molar ratio=25.

Forming the Zeolite by Mixing-Extrusion

An aqueous suspension containing the zeolite is mixed in a high-shear system of the Ultra-Turrax type and is then subjected to ultrasonic treatment. Then the suspension is mixed with kaolin. The composition as percentage dry weight is 40% zeolite and 60% kaolin. After obtaining a homogeneous paste the latter is extruded through a die and the extrudates are dried for 12 hours at 120° C. and calcined under an air flow for 2 hours at 550° C.

Post-Treatments

The extrudates are then subjected to a steam treatment for 24 hours under a flow of 6% of steam at a flow rate of 1 litre per hour per gram of extrudates under NTP conditions at 700° C. Then the latter are ground and sieved in order to retain the 40-140 μm fraction. The catalyst thus obtained is called NC2.

Example 3: Preparation of Catalyst C1 (According to the Invention)

Synthesis of Zeolite NU-86

The crude synthesized zeolite NU-86 is prepared according to Example 2 of patent EP 0 463768 A2 with quantities adjusted so as to obtain 50 grams of calcined zeolite. It first undergoes a so-called dry calcination at 550° C. under a flow of dry air for 9 hours. Then the solid obtained is subjected to three ion exchanges in a 10N solution of $NH_4NO_3$, at about 100° C. for 4 hours for each exchange. The solid thus obtained is referenced $NH_4$-NU-86 and has an Si/Al molar ratio=14 and an Na/Al molar ratio=0.0033. Its other physicochemical characteristics are presented in Table 1 below.

TABLE 1

| | Description of zeolite NU-86 | | |
|---|---|---|---|
| | X-ray diffraction | Adsorption | |
| Sample | Crystallinity (%) | S BET ($m^2/g$) | V(P/Po = 0.19) ml liquid $N_2$/g |
| $NH_4$-NU-86 | 100 | 450 | 0.19 |

The crystallites of zeolite $NH_4$-NU-86 are in the form of agglomerates the size of which varies from 0.2 μm to 2 μm.

Forming the Zeolite by Mixing-Extrusion

An aqueous suspension containing zeolite $NH_4$-NU-86 is mixed with boehmite PURAL SB3 and kaolin. The composition as percentage dry weight is 40% zeolite, 30% kaolin and 30% alumina. After obtaining a homogeneous paste the latter is extruded through a die and the extrudates are dried for 12 hours at 120° C. in a stove and calcined under an air flow for 2 hours at 550° C.

Post-Treatments

The extrudates are then subjected to steam treatment for 24 hours under a flow of 100% of steam at a flow rate of 1 litre per hour per gram of extrudates (NTP conditions) at 800° C. Then the latter are ground and sieved in order to retain the 40-140 μm fraction. The catalyst thus obtained is called C1.

Example 4: Preparation of Catalyst C2 (According to the Invention)

Forming the Zeolite by Atomization

An aqueous suspension containing zeolite NU-86 is mixed with Nyasil 20 and kaolin in a high-shear system of the Ultra-Turrax type. The percentage by dry weight of zeolite with respect to the total dry weight in the suspension is 40%. The suspension is then atomized. The catalyst obtained is dried at 120° C. for 12 hours. The grains obtained have a size between 40 and 140 μm.

Post-Treatments

The grains are then subjected to steam treatment for 24 hours under a flow of 100% of steam at a flow rate of 1 litre per hour per gram of extrudates (NTP conditions) at 800° C. The catalyst thus obtained is called C2.

Example 5: Preparation of Catalyst C3 (According to the Invention)

The synthesis of zeolite NU-86 is the same as for catalyst C1.

Forming the Zeolite by Mixing-Extrusion

An aqueous suspension containing zeolite $NH_4$-NU-86 is mixed in a high-shear system of the Ultra-Turrax type and is subjected to ultrasonic treatment. Then the suspension is mixed with kaolin. The composition as percentage dry weight is 40% zeolite and 60% kaolin. After obtaining a homogeneous paste the latter is extruded through a die and the extrudates are dried for 12 hours at 120° C. in a stove and calcined under an air flow for 2 hours at 550° C.

Post-Treatments

The extrudates are then subjected to steam treatment for 24 hours under a flow of 6 vol % of steam and 96 vol % of dry air with a total flow rate of 1 litre per hour per gram of extrudates (NTP conditions) at 700° C. Then the latter are ground and sieved in order to retain the 40-140 μm fraction. The catalyst thus obtained is called C3.

Example 6: Preparation of Catalyst C4 (According to the Invention)

The synthesis of zeolite NU-86 is the same as for catalyst C1.

Doping the Zeolite

Ammonium dihydrogen phosphate $((NH_4)H_2PO_4)$, used as phosphorus precursor, is dissolved in a volume of water corresponding to a V/W (volume of solution/weight of zeolite) of 10 ml/g. The solution is brought into contact with the catalyst at ambient temperature for 20 minutes in a rotary evaporator. Magnesium hydroxide $Mg(OH)_2$ is then added and stirring is maintained for 20 minutes. The pH is adjusted to between 7 and 8 with an ammonia solution and then the mixture is stirred for 20 minutes at 45° C. The solvent is then removed gently at 60° C. The catalyst is then dried for 2 hours in a stove at 100° C. and then calcined for 3 hours at 500° C. The quantities of precursors used are adjusted in order to obtain a quantity of phosphorus of 1.5% by weight and of magnesium of 0.6% by weight for the final catalyst after calcination.

Forming the Zeolite by Mixing-Extrusion-Grinding

An aqueous suspension containing zeolite $NH_4$-NU-86 is mixed in a high-shear system of the Ultra-Turrax type and is subjected to ultrasonic treatment. Then the suspension is mixed with kaolin. The composition as percentage dry weight is 40% zeolite and 60% kaolin. After obtaining a homogeneous paste the latter is extruded through a die and the extrudates are dried for 12 hours at 120° C. in a stove and calcined under an air flow for 2 hours at 550° C.

Post-Treatments

The extrudates are then subjected to steam treatment for 24 hours under a flow of 6 vol % of steam and 96 vol % of dry air with a total flow rate of 1 litre per hour per gram of extrudates (NTP conditions) at 700° C. Then the latter are ground and sieved in order to retain the 40-140 μm fraction. The catalyst thus obtained is called C4.

Example 7: Preparation of C5 (According to the Invention)

Synthesis of zeolite NU-86

Zeolite $NH_4$-NU-86 is prepared as in Example C1.

It is then subjected to hydrothermal treatment in the presence of 100% of steam at 650° C., for 4 hours. The zeolite is then treated with acid, using 7N nitric acid, at about 100° C., so as to extract the extra-network aluminium species formed in the hydrothermal treatment. The volume V of the nitric acid solution used (in ml) is equal to 10 times the weight W of dry zeolite NU-86 (V/W=10). The zeolite thus obtained is filtered and dried for 12 hours in a stove at 120° C. and then calcined for 4 hours at 550° C. under an air flow.

At the end of these treatments the zeolite H-NU-86 in the H form has an overall Si/Al atomic ratio equal to 25.

Forming the Zeolite by Mixing-Extrusion-Grinding

An aqueous suspension containing the zeolite $NH_4$-NU-86 obtained in the preceding step is mixed in a high-shear system of the Ultra-Turrax type and is subjected to ultrasonic treatment. Then the suspension is mixed with Nyasil 20 as silica precursor. The composition as percentage dry weight is 40% zeolite and 60% silica. After obtaining a homogeneous paste the latter is extruded through a die and the extrudates are dried for 12 hours at 120° C. in a stove and calcined under an air flow for 2 hours at 550° C.

Post-Treatments

The extrudates are then subjected to steam treatment for 24 hours under a flow of 6 vol % of steam and 96 vol % of dry air with a total flow rate of 1 litre per hour per gram of extrudates (NTP conditions) at 700° C. Then the latter are ground and sieved in order to retain the 40-140 μm fraction. The catalyst thus obtained is called C5.

The data for the examples are summarized in Table 2.

Summary Table 2

| | Dopant on zeolite | Steam treatment on zeolite | Treatment with acid | Forming | Steam treatment | Dopant on extrudates |
|---|---|---|---|---|---|---|
| NC1 ZSM-5 Si/Al = 25 | / | / | / | Extr + grinding $Al_2O_3$ + kaolin | 800° C. 24 h 100% $H_2O$ | / |
| NC2 ZSM-5 Si/Al = 25 | / | / | / | Dispersion Extr + grinding Kaolin | 700° C. 24 h 6% $H_2O$ | / |
| C1 NU-86 Si/Al = 14 | / | / | / | Extr + grinding $Al_2O_3$ + kaolin | 800° C. 24 h 100% $H_2O$ | / |
| C2 NU-86 Si/Al = 14 | / | / | / | Atomization | 800° C. 24 h 100% $H_2O$ | / |
| C3 NU-86 Si/Al = 14 | / | / | / | Dispersion Extr + grinding Kaolin | 700° C. 24 h 6% $H_2O$ | / |
| C4 NU-86 Si/Al = 14 | P, Mg | / | / | Dispersion Extr + grinding Kaolin | 700° C. 24 h 6% $H_2O$ | / |
| C5 NU-86 Si/Al = 14 | / | yes | Yes → Si/Al = 25 | Dispersion Extr + grinding Silica | 700° C. 24 h 6% $H_2O$ | / |

Example 8: Catalytic Tests

The following tests were carried out on a laboratory unit comprising a quartz reactor heated by an electric furnace with the temperature of which is monitored by a thermocouple placed in the catalyst bed. The weight of catalyst introduced into the reactor is 30 grams, representing a bed height of 22 cm when the latter is fluidized by 2×200 Nml/min of nitrogen. The catalyst is placed under an air flow at 680° C. to remove any trace of residual coke from a preceding test and then the air supply is stopped and the temperature is maintained at 680° C. under nitrogen. The naphtha feedstock consists of C6-C8 hydrocarbons, comprising 76% by weight of paraffins, 19.5% by weight of naphthenes and 4.5% by weight of aromatics. The feedstock has an initial boiling point of 37.6° C. and a final boiling point of 126.8° C. It is introduced at 1.2 bar absolute using a calibrated syringe pump to introduce 2.88 g of feedstock in 200 s. Nitrogen serving for fluidization of the catalytic system, and thus as diluent, is introduced at a rate of 15% by weight of the mixture (feedstock+nitrogen). The liquid and gaseous effluents are collected, quantified and qualified at the reactor outlet in order to establish a mass balance and a structure of the yield originating from cracking. The catalyst is collected in order to measure the level of coke.

Table 3 gives the yields by weight of ethylene, propylene, butene and BTX, as well as the propylene/ethylene ratio P/E, obtained in the naphtha cracking test for the catalysts not according to the invention NC1, NC2, and those according to the invention C1 to C5.

TABLE 3

|     | Yield C2= (% by weight) | Yield C3= (% by weight) | Yield C4= (% by weight) | Yield BTX (% by weight) | P/E |
| --- | --- | --- | --- | --- | --- |
| NC1 | 10.9 | 16.2 | 6.2 | 9.4 | 1.49 |
| NC2 | 16.5 | 18.4 | 5.7 | 14.0 | 1.11 |
| C1  | 12.3 | 18.2 | 6.3 | 10.2 | 1.48 |
| C2  | 17.3 | 19.3 | 6.1 | 13.2 | 1.12 |
| C3  | 17.2 | 19.5 | 6.2 | 15.2 | 1.13 |
| C4  | 17.4 | 20.7 | 6.5 | 15.7 | 1.19 |
| C5  | 17.3 | 20.4 | 6.9 | 13.6 | 1.18 |

Catalyst C1 based on NU-86 according to the invention makes it possible to obtain a better yield of light olefins, C2, C3, C4 and of BTX relative to catalyst NC1 based on ZSM-5 and prepared according to the same procedure.

Catalyst C3 based on NU-86 according to the invention makes it possible to obtain a better yield of light olefins, C2, C3, C4 and of BTX relative to catalyst NC2 based on ZSM-5 and prepared according to the same procedure.

Catalyst C4 based on NU-86 and doped with P and Mg according to the invention makes it possible to obtain a further improvement in the yields of light olefins relative to catalyst C3 according to the invention.

Catalyst C5 comprising a dealuminated zeolite NU-86 makes it possible to obtain a better yield of light olefins than C3 according to the invention in which the zeolite NU-86 had not been dealuminated.

Moreover, catalyst C5 comprising a dealuminated zeolite NU-86 having a Si/Al ratio=25 makes it possible to obtain a better yield of light olefins relative to NC1 and NC2 comprising a zeolite ZSM-5 also having a Si/Al ratio=25.

The use of zeolite NU-86 also allows production of predominantly propylene.

Table 4 shows the detailed results of the naphtha cracking tests on catalysts NC1 and C1.

Conversion is defined as the sum of the required products, i.e. olefins with 2, 3 and 4 carbon atoms, BTXs and the coke necessary for maintaining thermal equilibrium of the NCC unit.

TABLE 4

| Catalyst | | Catalyst NC1 (ZSM-5) | Catalyst C1 (NU-86) | Gain in points (% by weight)/ relative gain (%) |
| --- | --- | --- | --- | --- |
| Conversion | % by weight | 45.7 | 50.4 | |
| Dry gases | % by weight | 22.9 | 25.9 | |
| H2 | % by weight | 0.8 | 0.9 | |
| C1 | % by weight | 7.5 | 8.7 | |
| C2= | % by weight | 10.9 | 12.3 | 1.4/12.8 |
| C2 | % by weight | 3.7 | 4.0 | |
| LPG | % by weight | 25.2 | 27.9 | |
| C3 | % by weight | 1.8 | 2.2 | |
| C3= | % by weight | 16.2 | 18.2 | 2.0/12.3 |
| total C4 | % by weight | 0.9 | 1.1 | |
| iC4 | % by weight | 0.6 | 0.7 | |
| nC4 | % by weight | 0.3 | 0.4 | |
| total C4= | % by weight | 6.2 | 6.3 | 0.1/1.6 |
| iC4= | % by weight | 2.4 | 2.5 | |
| nC4= | % by weight | 3.8 | 3.8 | |
| C4== | % by weight | 0.2 | 0.1 | |
| PI-160 | % by weight | 48.2 | 41.9 | |
| 160-220 | % by weight | 0.8 | 0.9 | |
| PI-220 | % by weight | 48.9 | 42.8 | |
| BTX | % by weight | 9.4 | 10.2 | 0.8/8.5 |
| coke | % by weight | 2.9 | 3.4 | |
| P/E ratio | w/w | 1.49 | 1.48 | |

This demonstrates the advantage of NU-86, making it possible to obtain a conversion to light olefins (ethylene+propylene+butenes) and BTX (benzene+toluene+xylenes) greater than 4.25 pts relative to a ZSM-5, or a relative gain of more than 10% on the sum of these compounds.

The invention claimed is:

1. A process comprising catalytic cracking of a gasoline feedstock having a paraffin content of 50-90% by weight with respect to the feedstock to produce light olefins, the catalytic cracking comprising contacting said gasoline feedstock with a catalyst comprising zeolite NU-86, alone or in a mixture with at least one other zeolite, at a temperature between 550 and 700° C. and with a contact time of the gasoline feedstock on said catalyst between 10 milliseconds and 100 seconds.

2. The process according to claim 1, in which the gasoline feedstock comprises hydrocarbon compounds having 4 to 15 carbon atoms.

3. The process according to claim 1, in which said gasoline feedstock has an initial boiling point of 20 to 100° C. and a final boiling point of 100 to 250° C.

4. The process according to claim 1, in which said gasoline feedstock has an olefin content of 0 to 17% by weight, a naphthene content of 10 to 50% by weight, and an aromatic content of 0 to 30% by weight, wherein the percentages by weight of feedstock contents are expressed with respect to a total weight of said feedstock, and wherein a sum of the paraffin content, the olefin content, the naphthene content and the aromatic content is equal to 100%.

5. The process according to claim 1, in which said gasoline feedstock is contacted with said catalyst in a reactor operating with a fixed bed.

6. The process according to claim 1, in which said gasoline feedstock is introduced into a reactor in a mixture with a diluent, wherein said diluent is an inert gas or steam.

7. The process according claim 1, in which said catalyst comprises zeolite NU-86 in a mixture with at least one other zeolite selected from the group consisting of ZSM-5, ZSM-11, beta, Y, ferrierite, ZSM-22, ZSM-23, EU-1 zeolite, and a mixture thereof.

8. The process according to claim 7, in which said catalyst has a content of NU-86 of 60 to 99% by weight with respect to a total weight of zeolites contained in said mixture with at least one other zeolite.

9. The process according to claim 1, in which the catalyst comprises at least one binder selected from the group consisting of alumina, silica, silica-alumina, magnesia, titanium oxide, zirconia, a clay, boron oxide, and a mixture thereof.

10. The process according to claim 9, wherein the at least one binder is selected from the group consisting of silica, silica-alumina, a clay, and a mixture thereof.

11. The process according to claim 1, in which the catalyst comprises:
from 20 to 80% by weight of at least one binder,
from 20 to 80% by weight of zeolite NU-86,
from 0 to 50% by weight of at least one zeolite selected from the group consisting of ZSM-5, ZSM-11, beta, Y, ferrierite, ZSM-22, ZSM-23, EU-1, and a mixture thereof, and
from 0 to 12% by weight of at least one doping element, wherein the percentages of the binder, zeolite(s) and doping element are being expressed with respect to a total weight of said catalyst and wherein a sum of the binder, zeolite(s) and doping element is equal to 100%.

12. The process according claim 1, in which one or more dopants selected from the group consisting of phosphorus, magnesium, sodium, potassium, calcium, iron, boron, manganese, lanthanum, cerium, titanium, tungsten, molybdenum, copper, zirconium, gallium, and a mixture thereof are introduced into said catalyst.

13. The process according to claim 12, in which said dopant is introduced on the at least one zeolite, alone or in a mixture with at least one other zeolite, prior to forming.

14. The process according to claim 12, in which the one and more dopants are introduced on the catalyst after forming.

15. The process according to claim 1, carried out at a temperature of 600 to 680° C., at an absolute pressure of 1.2 bar, and with a contact time of the feedstock on said catalyst of 100 milliseconds to 4 seconds.

16. The process according to claim 1, in which said gasoline feedstock is contacted with said catalyst in a reactor operating with a moving bed.

17. The process according to claim 1, in which said gasoline feedstock is contacted with said catalyst in a reactor operating with a fluidized bed.

* * * * *